United States Patent [19]

Williams

[11] Plant 4,036

[45] Apr. 5, 1977

[54] ROSE PLANT

[76] Inventor: Ernest D. Williams, 1510 Lebanon Ave., Dallas, Tex. 75208

[21] Appl. No.: 676,569

[22] Filed: Apr. 13, 1976

[51] Int. Cl.[2] ..... A01H 5/00

[52] U.S. Cl. ..... Plt./7

[58] Field of Search ..... Plt./7

*Primary Examiner*—Robert E. Bagwill

EXEMPLARY CLAIM

1. A new and distinct variety of miniature rose plant of hardy, dwarf, rounded, much branched, bush type, substantially as illustrated and described, characterized by buds and flowers resembling Windy City (miniature — U.S. Plant Pat. No. 3,792) in general form and size; the bud and flower color resembling the variety Little Darling (Floribunda — U.S. Plant Pat. No. 1,581, expired) in the blending of yellow, pink and red but usually with more contrast, the general color effect being, yellow with contrasting shades of red; the small buds having rather long sepals with extra foliaceous parts; and further characterized by a plant which is vigorous and compact with abundant disease resistant foliage, a plant which is easily propagated from cuttings, an abundance of bloom with flowers borne singly or several to the stem in loose clusters.

1 Drawing Figure

1

The present invention relates to a new and distinct variety of hardy, dwarf, bush type rose plant of the miniature class; the variety being primarily characterized — as to novelty — by buds and flowers with a multi - color effect being basically yellow with petal tips overlaid with varying shades of red.

The variety is further characterized by:

An abundance of bloom, with flowers borne singly or several to stem in loose clusters.

Moderate fragrance.

A plant which is vigorous, of rounded upright shape, and with semi-glossy, small foliage with pointed leaflets; the flowers and foliage being similar in size to the variety Windy City (miniature — U.S. Plant Pat. No. 3,792). The plant has a normal average height of 12 to 14 inches at maturity but can be easily maintained at lesser height by occasional trimming.

A plant which grows and blooms satisfactorily both in greenhouse and outdoors; is a good plant for growing in pots; and provides excellent garden decoration as well as cut flowers.

The present variety of minature rose was originated by me at my nursery located at Dallas, Tex., under conditions of careful control and observation, as a cross between an un-named seedling (orange colored floribunda — not patented) as the seed parent and Over the Rainbow (miniature — U.S. Plant Pat. No. 3,472) as the pollen parent.

Subsequent to origination of the variety I successfully asexually reproduced it in my nursery located as aforesaid, by cuttings; the reproductions having run true in all respects.

The color photograph illustrates the variety including foliage, buds and flowers.

Referring now specifically to the new and distinct variety of miniature rose plant, the following is a detailed description thereof in outline; all major color plate identifications being by reference to the R.H.S. Color Chart, except where common terms of color definition are employed.

Type: Hardy; dwarf; bush; seedling; greenhouse; outdoors; cut flowers; garden decoration; potted plant.

2

Class: Miniature. Variety name: Sassy Lassy.

Flowers:

*Continuity.*—Continuous.

*Fragrance.*—Moderate.

Flowers borne: Singly and several together (3 to 5) on normal strength medium length stems.

Quality of Bloom: Abundant both outside and in greenhouse.

Bud:

*Penduncle.*—Medium length; slender; erect; medium green (often tinted bronze, outdoors) with numerous soft hairs.

*Before calyx breaks.*—Size — small. Form — medium long; pointed with foliaceous appendages and numerous tiny short hairs on surface of the bud; with foliaceous parts extending beyond the tip of the bud equal to one-half or more of its length. Color — medium green, often tinted bronze (outdoors).

*As calyx breaks.*—Color — Yellow.

*As first petal opens.*—Yellow, shaded with red (or pink) on outer half of upper surface of petal; size — small. Form: medium length; pointed; becoming rounded or high centered.

*Opening.*—opens well in all weather.

Bloom:

*Size when fully open.*—Small, averaging, 35 - 38 mm (up to 1½ inches).

*Petalage.*—Very double — up to 40 or more petals (plus several narrow petaloids) arranged regularly.

*Form.*—Slightly cupped at first, with petals rolled loosely outward, and later at maturity becoming high centered with petals being loosely rolled outward and with outer petals often rolled downward.

Petals: Thick; satiny both inside and outside.

*Shape.*—Outside petals oval (broad lanceolate with rounded tip); intermediate — broad lanceolate with rounded tip; inside narrow lanceolate.

Color: Newly opened flower from a plant grown outdoors (September 1975), Dallas, Tex.

*Outside petal.*—Outside surface — near yellow 12B or C overlaid with red (near 55A) on outer half of petal surface.

*Intermediate petal.*—Outside surface — similar to outside petal; inside surface — similar to outside petal.

*Inner petal.*—Outside surface — essentially same as intermediate petal; inside surface — similar to intermediate petal.

General color effect newly opened flower — yellow and red (or orange red). Three days open — usually red color is lighter (nearing 56A) and the yellow becomes progressively lighter. Behavior — Flower color is reasonably lasting even in warm weather. Flower longevity (June 1975) — bush in garden or pot — 5 – 7 days. Cut flowers at living room temperature — 3 to 5 days.

Reproductive Organs:

*Stamens.*—Moderate number.

*Filaments.*—Medium length; yellow.

*Pollen.*—Some.

*Pistils.*—Average.

*Styles.*—Medium length; bunched.

*Ovaries.*—All enclosed in calyx.

*Hips.*—None.

*Sepals.*—Permanent; spear shaped; recurved.

*Seed.*—None.

Foliage:

*Leaves.*— Compound of five leaflets (sometimes 7); abundant; small to moderately small; leathery; semi-glossy.

*Leaflets.*—Shape: broad lanceolate; apex acute; base rounded or rounded acute. Margin serrate. Color: normal green; new growth often tinted bronze. Rachis: medium strength, upper side slightly hairy, grooved, underside sparsely thorny. Stipules: medium length; narrow; short to medium length points, turning out at an angle of about 45° or more.

Growth:

*Habit.*—Dwarf; bushy; rounded; much branched. Growth — free; vigorous. Canes — medium; slender.

*Main Stems.*—Color — medium green. Thorns: sparsely thorny: medium length; hooked slightly downward; Color — medium brown. Prickles — none. Hairs — none.

*Branches.*—Color: medium green. Thorns: few; short; hooked slightly downward; medium length oval base. Prickles; none. Hairs — none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, rounded, much branched, bush type, substantially as illustrated and described, characterized by buds and flowers resembling Windy City (miniature — U.S. Plant Pat. No. 3,792) in general form and size; the bud and flower color resembling the variety Little Darling (Floribunda — U.S. Plant Pat. No. 1,581, expired) in the blending of yellow, pink and red but usually with more contrast, the general color effect being, yellow with contrasting shades of red; the small buds having rather long sepals with extra foliaceous parts; and further characterized by a plant which is vigorous and compact with abundant disease resistant foliage, a plant which is easily propagated from cuttings, an abundance of bloom with flowers borne singly or several to the stem in loose clusters.

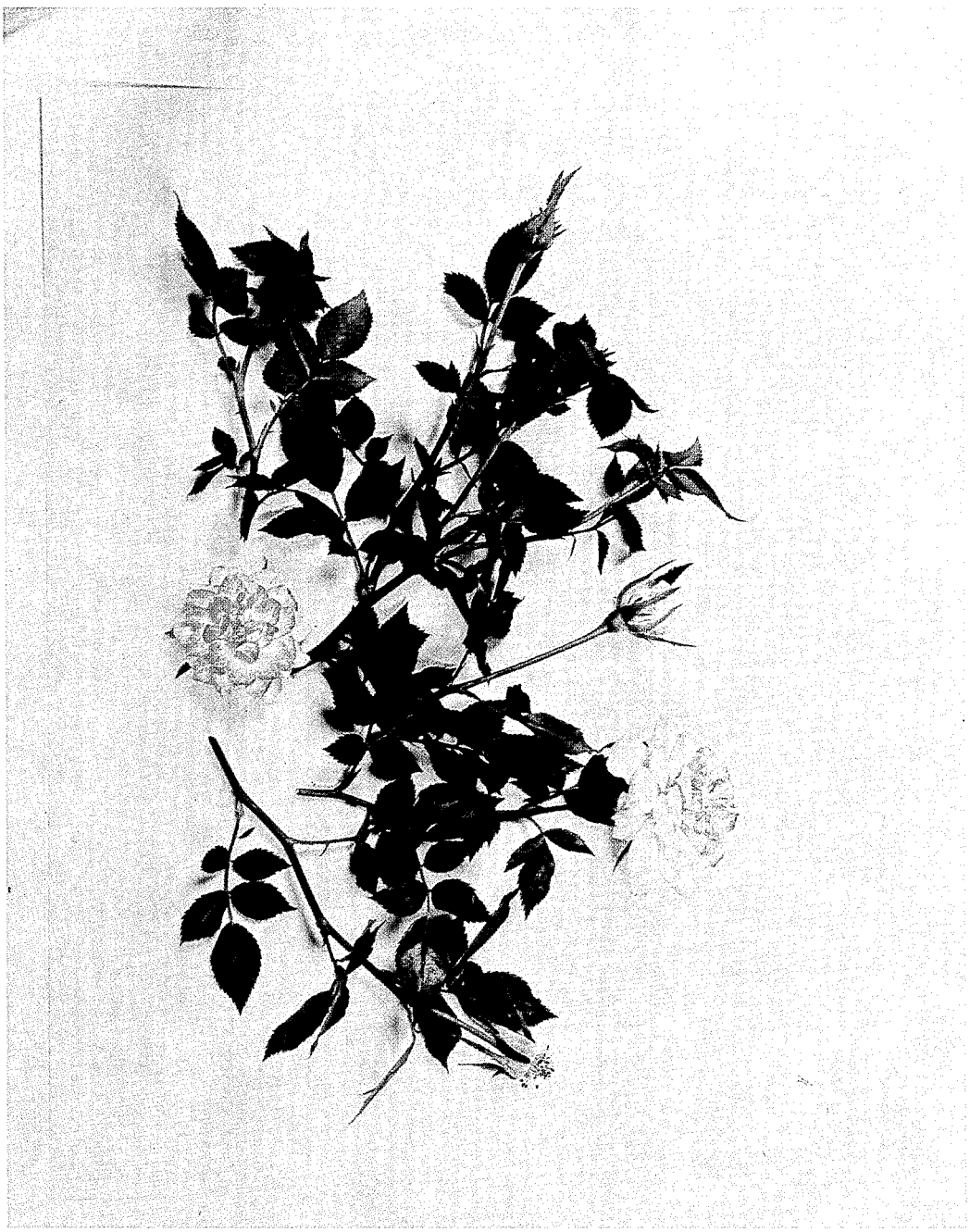

* * * * *